United States Patent [19]

Angerbauer et al.

[11] Patent Number: 5,418,243
[45] Date of Patent: May 23, 1995

[54] SUBSTITUTED 4-PHENYL-PYRIDONES AND 4-PHENYL-3-ALKOXYPYRIDINES

[75] Inventors: Rolf Angerbauer; Peter Fey; Walter Hübsch, all of Wuppertal; Thomas Philipps, Cologne; Hilmar Bischoff, Wuppertal; Hans-Peter Krause, Schwelm; Jörg Peterson-von Gehr, Bochum; Delf Schmidt, Wuppertal, all of Germany

[73] Assignee: Bayer Aktiengesellschaft, Leverkusen, Germany

[21] Appl. No.: 166,775

[22] Filed: Dec. 14, 1993

[30] Foreign Application Priority Data

Dec. 21, 1992 [DE] Germany ............... 42 43 278.2
Jun. 28, 1993 [DE] Germany ............... 43 21 421.5

[51] Int. Cl.$^6$ .................. A61K 31/44; C07D 213/64
[52] U.S. Cl. .................................. 514/345; 546/24; 546/290; 514/89
[58] Field of Search ............ 546/290, 24; 514/345, 514/89

[56] References Cited

U.S. PATENT DOCUMENTS

| | | | |
|---|---|---|---|
| 4,083,983 | 4/1978 | Durant et al. | 514/345 |
| 4,154,838 | 5/1979 | Durant et al. | 514/345 |
| 4,156,727 | 5/1979 | Durant et al. | 514/345 |
| 4,215,126 | 7/1980 | Durant et al. | 514/345 |
| 4,684,477 | 8/1987 | Sugimori et al. | 546/290 |
| 4,916,239 | 4/1990 | Treiber | 549/292 |
| 4,988,711 | 1/1991 | Angerbauer et al. | 514/326 |
| 5,032,602 | 7/1991 | Fey et al. | 514/345 |
| 5,064,841 | 11/1991 | Angerbauer et al. | 514/336 |
| 5,138,090 | 8/1992 | Fey et al. | 560/59 |

FOREIGN PATENT DOCUMENTS 0373423  6/1990  European Pat. Off. .

OTHER PUBLICATIONS

J. Med. Chem., 1990, vol. 33, pp. 52–60; "Synthesis and Biological Activity of New HGM–CoA Reductase Inhibitors . . . ", G. Beck.

Primary Examiner—C. Warren Ivy
Assistant Examiner—A. A. Owens
Attorney, Agent, or Firm—Sprung, Horn, Kramer & Woods

[57] ABSTRACT

Substituted 4-phenyl-pyridones and 4-phenyl-2-alkoxypyridines are prepared by reducing corresponding 4-phenyl-pyridone and 4-phenyl-2-alkoxypyridine derivatives. The substituted 4-phenyl-pyridones and 4-phenyl-2-alkoxypyridines can be employed as active compounds in medicaments, in particular for the treatment of hyperlipoproteinaemia.

8 Claims, No Drawings

SUBSTITUTED 4-PHENYL-PYRIDONES AND 4-PHENYL-3-ALKOXYPYRIDINES

The invention relates to substituted 4-phenyl-pyridones and 4-phenyl-2-alkoxypyridines, processes for their preparation, and their use in medicaments.

It is known that lactone derivatives isolated from fungal cultures are inhibitors of 3-hydroxy-3-methylglutaryl coenzyme A reductase (HMG-CoA reductase) [Mevinolin, EP 22 478; U.S. Pat. No. 4,231,938].

It is additionally known that pyridine-substituted dihydroxyheptenoic acids are inhibitors of HMG-CoA reductase [EP 325 130; EP 307 342; EP 306 929].

The present invention relates to substituted 4-phenyl-pyridones and 4-phenyl-2-alkoxypyridines of the general formula (I)

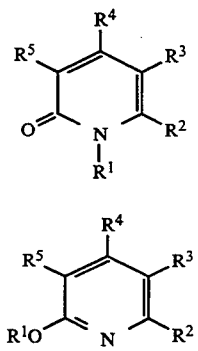

in which

R$^1$ represents straight-chain or branched alkyl having up to 8 carbon atoms,

R$^2$ represents cycloalkyl having 3 to 7 carbon atoms, or represents straight-chain or branched alkyl having up to 8 carbon atoms, R$^3$ represents a radical of the formula

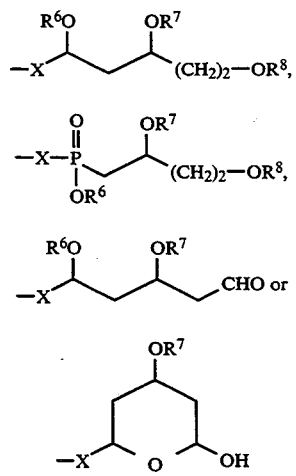

in which

X denotes the group —CH$_2$—CH$_2$—, —CH=CH— or —C≡C—, and

R$^6$, R$^7$ and R$^8$ are identical or different and denote hydrogen or a radical of the formula —CO—R$^9$ or —COOR$^{10}$, in which R$^9$ and R$^{10}$ are identical or different and denote straight-chain or branched alkyl having up to 8 carbon atoms, or phenyl, or R$^6$ and R$^7$ together form a radical of the formula

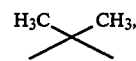

R$^4$ represents phenyl which is optionally substituted up to 2 times by identical or different halogen, trifluoromethyl, methoxy, phenoxy or straight-chain or branched alkyl having up to 8 carbon atoms, R$^5$ has the abovementioned meaning of R$^3$ and is identical to or different from this, or represents hydrogen, cyano, carboxyl or straight-chain or branched alkoxycarbonyl having up to 8 carbon atoms, or represents straight-chain or branched alkyl having up to 8 carbon atoms, which is optionally substituted by halogen, hydroxyl, by straight-chain or branched alkoxy having up to 8 carbon atoms, or by a group of the formula —O—(CH$_2$)$_a$—R$^{11}$ or —O—CO—R$^{12}$, in which a denotes a number 0 or 1, R$^{11}$ denotes phenyl or benzyl, each of which is optionally substituted up to 2 times in the aromatic system by identical or different halogen, trifluoromethyl, cyano, nitro or straight-chain or branched alkyl having up to 6 carbon atoms, R$^{12}$ has the abovementioned meaning of R$^{11}$ and is identical to or different from this, or denotes straight-chain or branched alkyl having up to 8 carbon atoms, or R$^5$ represents a radical of the formula —CH=N—O—R$^{13}$, in which R$^{13}$ has the abovementioned meaning of R$^{12}$ and is identical to or different from this.

Depending on the side chains mentioned under R$^3$ and/or R$^5$, the compounds according to the invention in each case have 1 or 2 asymmetric carbon atoms, to which the radicals —OR$^6$ and —OR$^7$ are bonded. They can therefore exist in various stereochemical forms.

The invention relates both to the individual isomers and to their mixtures. Depending on the relative position of the radicals —OR$^6$/—OR$^7$, the substances according to the invention can thus be present in the erythro configuration or in the threo configuration.

This will be illustrated by way of example for the substituents R$^3$/R$^5$ having the meaning a) as follows:

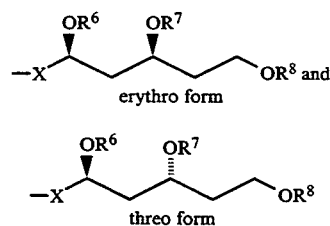

Two enantiomers exist in turn in each case both of the substances in the threo and in the erythro configuration. The erythro forms are preferred in each case.

Moreover, on account of the double bond (X=—CH=CH—), the substances according to the invention can be present in the E configuration or the Z configuration. Those compounds which have the E configuration are preferred.

In addition, the aldehyde radicals (subst. (c)) are in each case in equilibrium with the corresponding hydroxypyrans (subst. (d)).

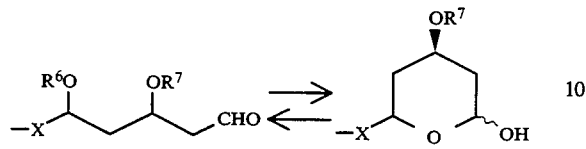

Preferred compounds of the general formula (I) are those in which $R^1$ represents straight-chain or branched alkyl having up to 6 carbon atoms, $R^2$ represents cyclopropyl, cyclopentyl or cyclohexyl, or represents straight-chain or branched alkyl having up to 6 carbon atoms, $R^3$ represents a radical of the formula

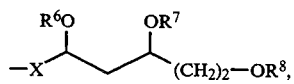

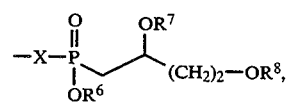

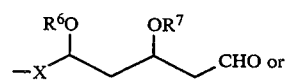

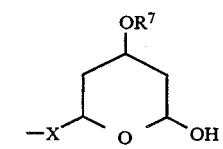

in which

X denotes the group —CH$_2$—CH$_2$—, —CH=CH— or —C≡C—, $R^6$, $R^7$ and $R^8$ are identical or different and denote hydrogen or a radical of the formula —CO—$R^9$ or —COO—$R^{10}$, in which $R^9$ and $R^{10}$ are identical or different and denote straight-chain or branched alkyl having up to 6 carbon atoms, or phenyl, or $R^6$ and $R^7$ together form a radical of the formula

$R^4$ represents phenyl which is optionally substituted up to 2 times by identical or different fluorine, chorine, bromine, trifluoromethyl or straight-chain or branched alkyl having up to 6 carbon atoms, $R^5$ has the abovementioned meaning of $R^3$ and is identical to or different from this, or represents hydrogen, cyano, carboxyl or straight-chain or branched alkoxycarbonyl having up to 6 carbon atoms, or represents straight-chain or branched alkyl having up to 6 carbon atoms, which is optionally substituted by fluorine, chlorine, bromine, hydroxyl or by straight-chain or branched alkoxy having up to 6 carbon atoms, or which is substituted by a group of the formula —O—(CH$_2$)$_a$—$R^{11}$ or —O—CO—$R^{12}$, in which a denotes a number 0 or 1, and $R^{11}$ denotes phenyl or benzyl, each of which is optionally substituted in the aromatic system by fluorine, chlorine, bromine, trifluoromethyl, cyano, nitro or straight-chain or branched alkyl having up to 4 carbon atoms, $R^{12}$ has the abovementioned meaning of $R^{11}$ and is identical to or different from this, or denotes straight-chain or branched alkyl having up to 6 carbon atoms, or $R^5$ represents a radical of the formula —CH=N—O—$R^{13}$, in which $R^{13}$ has the abovementioned meaning of $R^{12}$ and is identical to or different from this.

Particularly preferred compounds of the general formula (I) are those in which $R^1$ represents straight-chain or branched alkyl having up to 4 carbon atoms, $R^2$ represents cyclopropyl or represents straight-chain or branched alkyl having up to 4 carbon atoms, $R^3$ represents a radical of the formula

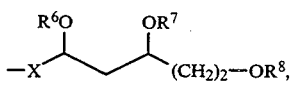

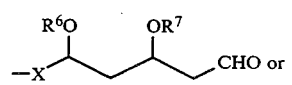

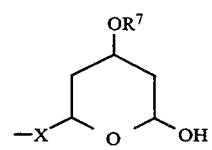

in which

X denotes the group CH$_2$—CH$_2$— or —CH=CH—, $R^6$, $R^7$ and $R^8$ are identical or different and denote hydrogen or a radical of the formula —CO—$^9$, in which $R^9$ denote straight-chain or branched alkyl having up to 4 carbon atoms, $R^4$ represents phenyl which is optionally substituted by fluorine, trifluoromethyl or by straight-chain or branched alkyl having up to 4 carbon atoms, $R^5$ has the abovementioned meaning of $R^3$ and is identical to or different from this, or represents hydrogen or represents straight-chain or branched alkyl having up to 4 carbon atoms, which is optionally substituted by hydroxyl or by straight-chain or branched alkoxy having up to 4 carbon atoms.

Very particularly preferred compounds of the general formula (I) are those in which $R^1$ represents straight-chain or branched alkyl having up to 4 carbon atoms, $R^2$ represents cyclopropyl or represents straight-chain or branched alkyl having up to 4 carbon atoms, $R^3$ represents a radical of the formula

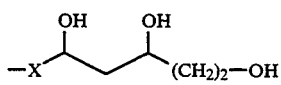

in which

X denotes the group —CH$_2$—CH$_2$— or —CH=CH—,

R$^4$ represents phenyl which is optionally substituted by fluorine, and

R$^5$ has the abovementioned meaning of R$^3$ or represents straight-chain or branched alkyl having up to 4 carbon atoms, which is optionally substituted by hydroxyl or alkoxy having up to four carbon atoms.

Especially preferred compounds of the general formula (I) according to the invention are those in which R$^1$ represents methyl and R$^3$ represents the radical of the formula

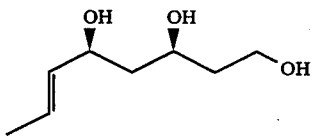

A process for the preparation of the compounds of the general formula (I) according to the invention has additionally been found, which is characterized in that pyridones or 2-alkoxypyridines of the general formula (II)

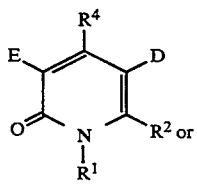 (IIa)

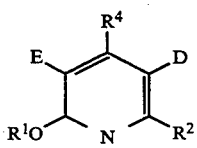 (IIb)

in which

R$^1$, R$^2$ and R$^4$ have the meaning indicated and

D represents a radical of the formula

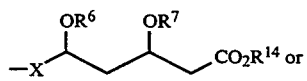

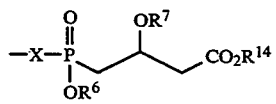

in which

A, B, R$^6$ and R$^7$ have the meaning indicated

R$^{14}$ represents C$_1$-C$_6$-alkyl and

E either also has the abovementioned meaning of D or the abovementioned meaning of R$^5$, are reduced in inert solvents, under a protective gas atmosphere, if appropriate via the aldehyde step, using reducing agents, and in the case in which —X— represents the —CH$_2$—CH$_2$— group, the ethene group (X=—CH=CH—) or the ethine group (X=—C≡C—) is hydrogenated stepwise according to customary methods and, if appropriate, the isomers are separated.

The process according to the invention can be illustrated by way of example by the following reaction equation:

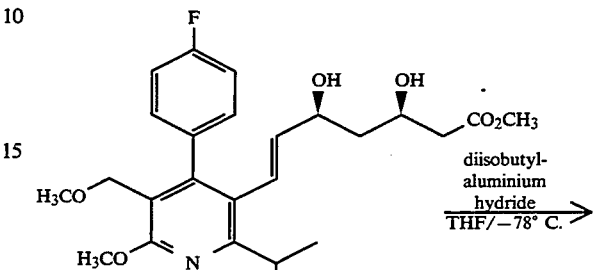

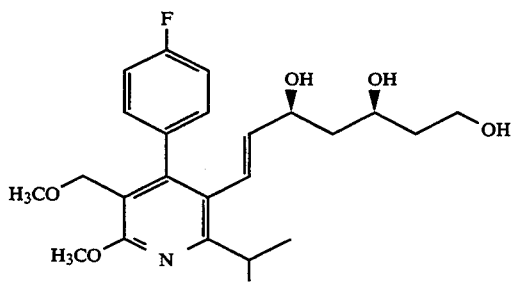

In general, suitable solvents for the reduction are the customary organic solvents. Ethers such as diethyl ether, tetrahydrofuran or dioxane are preferred. Tetrahydrofuran is particularly preferred.

Suitable reducing agents are complex metal hydrides, such as, for example, lithium aluminium hydride, sodium cyanoborohydride, sodium aluminium hydride, diisobutylaluminium hydride or sodium bis-(2-methoxyethoxy)dihydroaluminate. Diisobutylaluminium hydride is preferred.

In general, the reducing agent is employed in an amount from 4 mol to 10 mol, preferably from 4 mol to 5 mol, relative to 1 mol of the compounds of the general formula (II).

In general, the reduction proceeds in a temperature range from −78° C. to +50° C., preferably from −78° C. to 0° C., particularly preferably at −78° C., in each case depending on the choice of the reducing agent and solvent.

In general, the reduction proceeds at normal pressure, but it is also possible to work at elevated or reduced pressure.

The cyclization of the aldehydes to give the corresponding hydroxy-pyrans is in general carried out at room temperature or by heating in inert organic solvents, if appropriate in the presence of molecular sieve.

Suitable solvents in this case are hydrocarbons such as benzene, toluene, xylene, mineral oil fractions, or tetralin or diglyme or triglyme. Benzene, toluene or xylene is preferably employed. It is also possible to employ mixtures of the solvents mentioned. Hydrocarbons, in particular toluene, in the presence of molecular sieve are particularly preferably used.

The cyclization is in general carried out in a temperature range from −40° C. to +100° C., preferably from −25° C. to +50° C.

The hydrogenation of the double bond is carried out by customary methods using hydrogen in the presence of noble metal catalysts, such as, for example, Pd/C, Pt/C or Raney nickel in one of the abovementioned solvents, preferably in alcohols such as, for example, methanol, ethanol or propanol, in a temperature range from −20° C. to +100° C., preferably from 0° C. to +50° C., at normal pressure or elevated pressure.

The reduction of the triple or double bond is optionally also carried out during the abovementioned reduction of the ester group.

The compounds of the general formula (II) in which D and/or E represent the radical of the formula

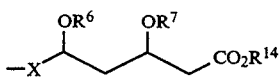

are prepared by reducing ketones of the general formulae IIIa and b

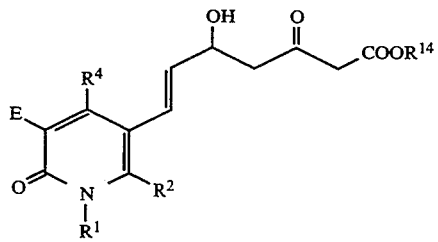

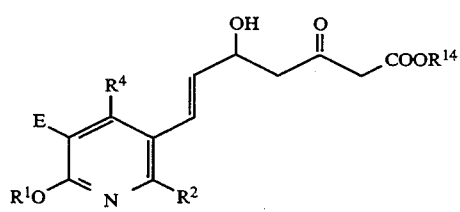

in which $R^1$ to $R^4$ and $R^{14}$ have the abovementioned meaning and, if appropriate, separating isomers.

The reduction can be carried out using the customary reducing agents, preferably using those which are suitable for the reduction of ketones to hydroxy compounds. Particularly suitable in this case is reduction using metal hydrides or complex metal hydrides in inert solvents, if appropriate in the presence of a trialkylborane. Preferably, the reduction is carried out using complex metal hydrides such as, for example, lithium borohydride, sodium borohydride, potassium borohydride, zinc borohydride, lithium trialkylborohydrides, sodium trialkylborohydrides, sodium cyanoborohydride or lithium aluminium hydride. The reduction is very particularly preferably carried out using sodium borohydride, in the presence of triethylborane.

Suitable solvents in this case are the customary organic solvents which do not change under the reaction conditions. These preferably include ethers such as, for example, diethyl ether, dioxane, tetrahydrofuran or dimethoxyethane, or halogenohydrocarbons such as, for example, dichloromethane, trichloromethane, tetrachloromethane or 1,2-dichloroethane or hydrocarbons such as, for example, benzene, toluene or xylene. It is also possible to employ mixtures of the solvents mentioned.

The reduction of the ketone group to the hydroxy group is particularly preferably carried out under conditions in which the other functional groups, such as, for example, the alkoxycarbonyl group, are not changed. Particularly suitable for this is the use of sodium borohydride as a reducing agent, in the presence of triethylborane in inert solvents such as, preferably, ethers.

The reduction is in general carried out in a temperature range from −80° C. to +30° C., preferably from −78° C. to 0° C.

The process according to the invention is in general carried out at normal pressure. However, it is also possible to carry out the process at reduced pressure or at elevated pressure (e.g. in a range from 0.5 to 5 bar).

In general, the reducing agent is employed in an amount of from 1 to 2 mol, preferably from 1 to 1.5 mol, relative to 1 mol of the keto compound.

Under the abovementioned reaction conditions, the carbonyl group is in general reduced to the hydroxy group without reduction of the double bond to the single bond taking place.

The ketones IIIa and b employed as starting substances are prepared by reacting aldehydes of the formulae IVa and b

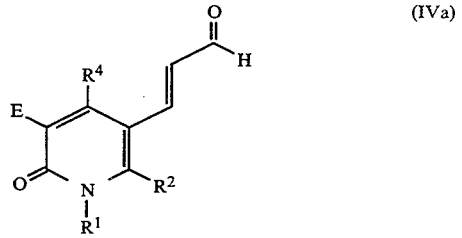

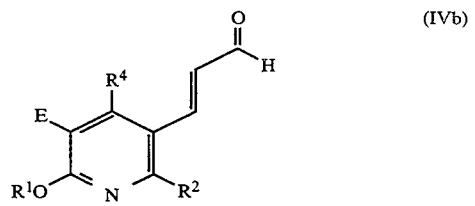

in which $R^1$ to $R^4$ have the meaning indicated, in inert solvents with acetoacetic esters of the general formula V

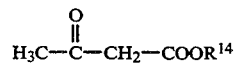

in which $R^{14}$ has the meaning indicated, in the presence of bases.

Possible bases in this case are the customary strongly basic compounds. These preferably include organolithium compounds such as, for example, n-butyllithium, sec-butyllithium, tert-butyllithium or phenyllithium or amides such as, for example, lithium diisopropylamide, sodium amide or potassium amide, or lithium hexamethyldisilylmide, or alkali metal hydrides such as sodium hydride or potassium hydride. It is also possible to employ mixtures of the bases mentioned. n-Butyllithium or sodium hydride or a mixture thereof is particularly preferably employed.

Additions of metal halides such as e.g. magnesium chloride, zinc chloride or zinc bromide are possibly advantageous. The addition of zinc halides is particularly preferred.

Suitable solvents in this case are the customary organic solvents which do not change under the reaction conditions. These preferably include ethers such as diethyl ether, tetrahydrofuran, dioxane or dimethoxyethane, or hydrocarbons such as benzene, toluene, xylene, cyclohexane, hexane or mineral oil fractions. It is also possible to employ mixtures of the solvents mentioned. Ethers such as diethyl ether or tetrahydrofuran are particularly preferred.

In general, the reaction is carried out in a temperature range from −80° C. to +50° C., preferably from −20° C. to room temperature.

In general, the process is carried out at normal pressure, but it is also possible to carry out the process at reduced pressure or at elevated pressure, e.g. in a range from 0.5 to 5 bar.

When carrying out the process, the acetoacetic acid ester is in general employed in an amount from 1 to 2 mol, preferably from 1 to 1.5 mol, relative to 1 mol of the aldehyde.

The acetoacetic acid esters of the formula (V) employed as starting substances are known or can be prepared by known methods.

Acetoacetic acid esters for the process according to the invention which may be mentioned are, for example: methyl acetoacetate, ethyl acetoacetate, propyl acetoacetate, isopropyl acetoacetate.

The preparation of the aldehydes of the general formula IVa or b employed as starting substances will be illustrated in the following by way of example for the compounds of the type (IVb).

[A]

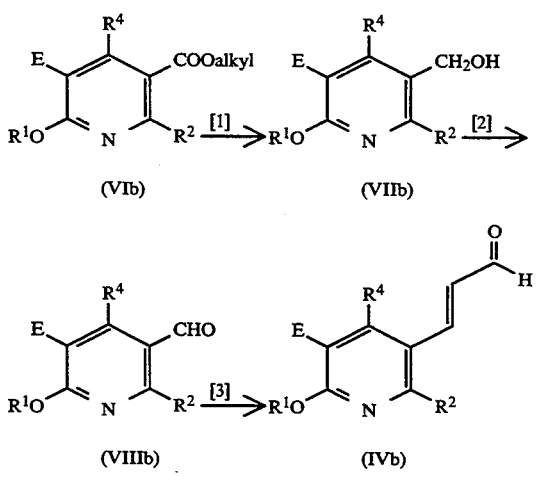

In this process, according to scheme A compounds of the formula VIb are reduced to the hydroxymethyl compounds in the first step [1] in inert solvents such as ethers, for example, diethyl ether, tetrahydrofuran or dioxane, preferably tetrahydrofuran, using metal hydrides as reducing agents, for example lithium aluminium hydride, sodium cyanoborohydride, sodium aluminium hydride, diisobutylaluminium hydride or sodium bis-(2-methoxyethoxy)-dihydroaluminate, in temperature ranges from −70° C. to +100° C., preferably from −70° C. to room temperature, or from room temperature to +70° C., depending on the reducing agent used. The reduction is preferably carried out using diisobutylaluminium hydride in tetrahydrofuran in a temperature range from −78° C. to room temperature. The hydroxymethyl compounds are oxidized to the aldehydes (XIII) in the second step [2] according to customary methods. The oxidation can be carried out, for example, using pyridinium chlorochromate, if appropriate in the presence of aluminium oxide, in inert solvents such as chlorohydrocarbons, preferably methylene chloride, in a temperature range from 0° C. to 60° C., preferably at room temperature, or else using trifluoroacetic acid/dimethyl sulphoxide according to the customary methods of Swern oxidation. The aldehydes (VIIb) are reacted to give the aldehydes (IVb) in the third step [3] using diethyl 2-(cyclohexylamino)-vinylphosphonate in the presence of sodium hydride in inert solvents such as ethers, for example diethyl ether, tetrahydrofuran or dioxane, preferably in tetrahydrofuran, in a temperature range from −20° C. to +40° C., preferably from −5° C. to room temperature.

The compounds of the formula (VIa, b) employed as starting substances in this process are new. They are possibly obtained in scheme B, shown by way of example for the alkoxy-dihydropyridines (IXb), by oxidation of 3,4-dihydropyridines. The oxidation of the dihydropyridines (IXb) to the pyridines (VIb), in which $R^{14}$ has the abovementioned meaning, can be carried out, for example, using chromium oxide or sodium nitrite in glacial acetic acid in a temperature range from −20° C. to +150° C., using nitric acid in aqueous suspension or using cerium salts, such as, for example, ammonium cerium nitrate, in a solvent mixture of acetonitrile and water. Preferably, acetonitrile and water are reacted with ammonium cerium nitrate in the mixture.

[B]

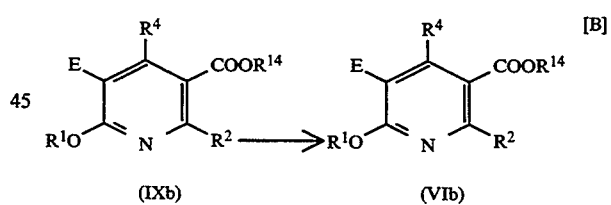

The 3,4-dihydropyridines of the general formula (IXa, b) employed in this process as starting substances are new.

In general, they are obtained by reaction of suitably substituted α,β-unsaturated carboxylic acid esters of the general formula (X) and appropriately substituted β-amino-α,β-unsaturated carboxylic acid esters of the general formula (XI) and subsequent alkylation.

The process can be carried out without solvent or in a high-boiling solvent such as, for example, ethylene glycol, either under basic conditions using alkali metal alkoxides, such as, for example sodium methoxide or potassium methoxide at room temperature to +200° C. or in glacial acetic acid at room temperature. Reaction with alkali metal alkoxides at +140° C. is preferred.

The reaction can be illustrated by the following reaction equation:

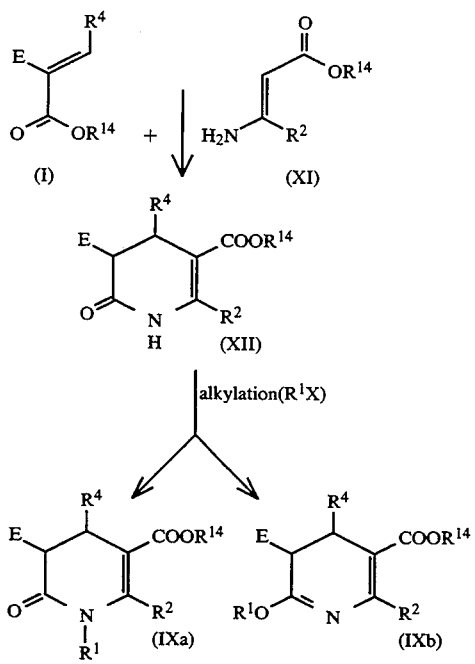

The alkylation is in general carried out using alkyl or benzyl halides in the presence of a base such as, for example, potassium carbonate, sodium hydride or an acid halide. The O-alkyl or O-acyl derivatives can be prepared in the presence of a base such as imidazole, pyridine or triethylamine.

In the case in which D and/or E represents the radical of the formula

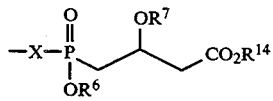

the compounds are mostly new.

However, they can be prepared in analogy to the process described above, by reducing, starting from the compounds of the general formulae

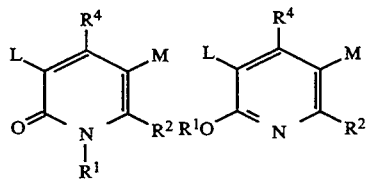

in which
R$^1$, R$^2$ and R$^4$ have the abovementioned meaning,
L and/or M represent the radical of the formula

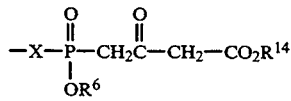

in which
—X—, R$^6$ and R$^{14}$ have the meaning indicated and represents C$_1$-C$_6$-alkyl.

[C] Suitable solvents in this case are in particular alcohols such as methanol, ethanol or propanol, preferably ethanol.

The reduction can be carried out using the customary reducing agents, preferably using those which are suitable for the reduction of ketones to hydroxy compounds. Particularly suitable in this case is reduction using metal hydrides or complex metal hydrides in inert solvents, if appropriate in the presence of a trialkylborane. Reduction is preferably carried out using complex metal hydrides such as, for example, lithium borohydride, sodium borohydride, potassium borohydride, zinc borohydride, lithium trialkylborohydride or lithium aluminium hydride. Reduction is very particularly preferably carried out using sodium borohydride, in the presence of triethylborane.

The reduction in general proceeds in a temperature range from $-78°$ C. to $+50°$ C., preferably from $-78°$ C. to $+25°$ C. and at normal pressure.

The compounds of the general formula (III) are mostly new, but can be prepared in analogy to known methods [cf. DE 38 172 98 A; U.S. Pat. No. 5,091,378].

In the case of the enantiomerically pure compounds of the general formula (I), either the corresponding enantiomerically pure esters of the general formula (II) are employed, which can be obtained according to published processes by reaction of the racemic products with enantiomerically pure amines to give the corresponding diastereomeric amide mixtures, subsequent separation by chromatography or crystallization into the individual diastereomers and final hydrolysis [cf. German Offenlegungsschrift 40 40 026] or by separating the racemic end products by customary chromatographic methods.

The substituted 4-phenyl-pyridones and 4-phenyl-2-alkoxypyridines according to the invention and their isomeric forms have useful pharmacological properties which are superior in comparison to the prior art, in particular they are highly active inhibitors in vivo of 3-hydroxy3-methyl-glutaryl coenzyme A (HMG-CoA) reductase and, as a result of this, inhibitors of cholesterol biosynthesis. They can therefore be employed for the treatment of hyperlipoproteinaemia or arteriosclerosis. The active compounds according to the invention additionally cause a decrease in the cholesterol content in the blood.

The pharmacological action of the substances according to the invention was determined in the following test:

Biological test for HMG-CoA reductase inhibitors

Cholesterol is synthesized in the mammal body from acetate units. In order to measure hepatic cholesterol biosynthesis in vivo, radiolabelled $^{14}$C-acetate was administered to the animals and the content of $^{14}$C-cholesterol was later determined in the liver.

The substances to be investigated were tested for inhibition of hepatic cholesterol biosynthesis in vivo on male Wistar rats having a body weight between 140 and 160 g. For this purpose, the rats were weighed 18 h before oral administration of the substances, divided into groups of 6 animals (control group without substance loading of 8 animals) and fasted. The substances to be investigated were suspended in aqueous 0.75% strength tragacanth suspension using an Ultra-Turrax immediately before administration. Administration of the tragacanth suspension (control animals) or the substances suspended in tragacanth was carried out by means of a stomach tube. The animals were injected intraperitoneally with -C-acetate (12.5 μCi/animal) 2 h after oral substance administration.

A further 2 h later (4 h after substance administration), the animals were sacrificed and bled out by cutting the throat. The abdominal cavity was then opened and a liver sample of about 700 mg was removed for the determination of the $^{14}$C-cholesterol synthesized from $^{14}$C-acetate. The cholesterol was extracted by a modification of the method of Duncan et al. (J. Chromatogr. 162 (1979) 281–292). The liver sample was homogenized in a glass Potter in isopropanol. After shaking and subsequent centrifugation, the supernatant was treated with alcoholic KOH and the cholesterol ester was hydrolyzed. After hydrolysis, the total cholesterol was extracted by shaking with heptane and the supernatant was evaporated. The residue was taken up in isopropanol, transferred to scintillation tubes and made up with LSC cocktail. The $^{14}$C-cholesterol synthesized from $^{14}$C-acetate in the liver was measured in the liquid scintillation counter. The hepatic $^{14}$C-cholesterol content of the animals treated only with tragacanth was used as a control. The inhibitory activity of the substances is indicated in % of the synthesized hepatic $^{14}$C-cholesterol content of the tragacanth control animals (=100%).

TABLE 1

| Ex. No. | Acute inhibition of $^{14}$C-cholesterol biosynthesis in vivo in the rat liver Dose which inhibits hepatic $^{14}$C-cholesterol synthesis by 50% (μg/kg of body weight p.o.) |
|---|---|
| I | 8 |
| II | 8 |

The present invention also includes pharmaceutical preparations which, in addition to inert, non-toxic, pharmaceutically acceptable auxiliaries and excipients, contain one or more compounds of the general formula (I), or which consist of one or more active compounds of the formula (I), and processes for the production of these preparations.

The active compounds of the formula (I) should be present in these preparations in a concentration from 0.1 to 99.5% by weight, preferably from 0.5 to 95% by weight of the total mixture.

In addition to the active compounds of the formula (I), the pharmaceutical preparations can also contain other pharmaceutical active compounds.

The abovementioned pharmaceutical preparations can be prepared in a customary manner according to known methods, for example using the auxiliary(ies) or excipient(s).

In general, it has proven advantageous to administer the active compound(s) of the formula (I) in total amounts from about 0.1 μg/kg to about 100 μg/kg, preferably in total amounts of about 1 μg/kg to 50 μg/kg of body weight every 24 hours, if appropriate in the form of several individual doses, to achieve the desired result.

However, it may sometimes be advantageous to depart from the amounts mentioned, namely depending on the type and body weight of the subject to be treated, on individual behaviour towards the medicament, the nature and severity of the disease, the type of preparation and administration, and the time or interval at which administration takes place.

STARTING COMPOUNDS

EXAMPLE 1

Ethyl 3-amino-4-methyl-pent-2-en-oate

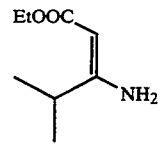

10.8 g of p-toluenesulphonic acid×4 H₂O are added to 500 g (3.16 mol) of ethyl isobutyrylacetate in 1,500 ml of toluene p.a., the mixture is saturated with ammonia gas while stirring at room temperature and allowed to stand overnight. It is then heated under reflux in a water separator and ammonia gas is continuously introduced until the calculated amount of water has separated (47 ml of water after reflux for 8 hours). The mixture is allowed to cool overnight, and the precipitate which has deposited is filtered off with suction and washed with toluene. The combined toluene phases are washed several times with water, dried using sodium sulphate, concentrated in vacuo and distilled in a high vacuum.

B.p.: 82°–85° C./1 mm Hg, Yield: 315 g (63.4% of theory, about 90% strength).

EXAMPLE 2

Methyl 1-carbomethoxy-2-(4-fluorophenyl)-propenoate

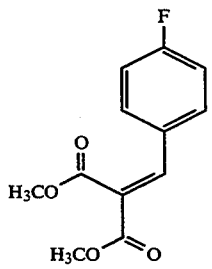

229 ml (2 mol) of dimethyl malonate, 223 ml (2 mol) of 4-fluorobenzaldehyde, 40 ml of piperidine and 103 ml of glacial acetic acid are heated under reflux in a water separator overnight in 1.5 l of cyclohexane. After cooling to room temperature, the mixture is taken up in ethyl acetate, washed with water, dried using sodium sulphate and distilled.

B.p.: 135° C.–140° C. (1 mm) Yield: 342.9 g (72% of theory).

EXAMPLE 3

3-Methyl 5-ethyl 3,4-dihydro-4-(4-fluorophenyl)-6-isopropyl-(1H)-pyrid-2-one-3,5-dicarboxylate

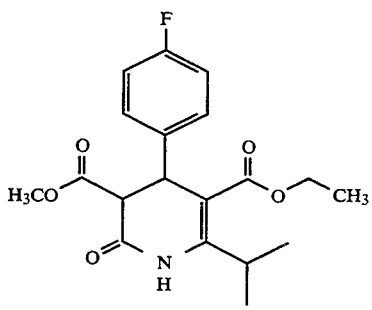

114.3 g (0.48 mol) of methyl 1-carbo-methoxy-2-(4-fluorophenyl)-propenoate, 75.4 g (0.48 mol) of ethyl 3-amino-4-methyl-pent-2-en-oate, 1 g of sodium methoxide and 5 ml of ethanol were stirred at a bath temperature of 140° C. for 60 h and the product was recrystallized from ethanol.

B.p.: 124° C. Yield: 115.4 g (66% of theory).

EXAMPLE 4

3-Methyl 5-ethyl 4-(4-fluorophenyl)-6-isopropyl-(1H)-pyrid-2-one-3,5-dicarboxylate

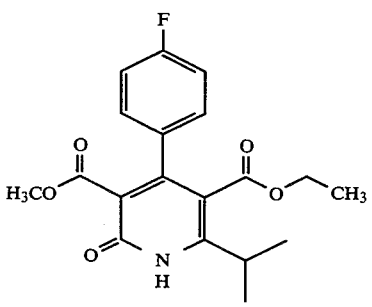

10.8 g (30 mmol) of the compound from Example 3 and 3.9 g (39 mmol) of chromium trioxide were heated under reflux in 100 ml of glacial acetic acid, a further 2 g (20 mmol) of chromium trioxide were added after 2 h and the mixture was heated under reflux overnight. The solvent was distilled off, the residue was dissolved in dilute hydrochloric acid, the solution was washed with ether, and the combined ether phases were washed with water, aqueous sodium hydrogen carbonate solution and water, dried using sodium sulphate and chromatographed on silica gel 70–230 mesh using ethyl acetate/petroleum ether 1:1.

Yield: 5.5 g (51% of theory). Melting point: 178° C.

EXAMPLE 5

3-Methyl 5-ethyl 4-(4-fluorophenyl)-6-isopropyl-2-methoxy-pyridine-3,5-dicarboxylate

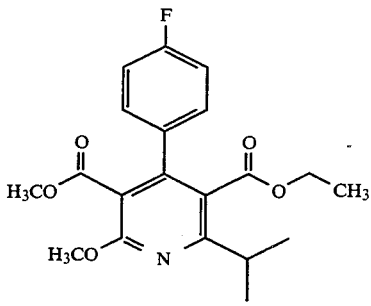

11.3 g (31 mmol) of the compound of Example 4, 1.2 g (50 mmol) of sodium hydride and 4 ml (62 mmol) of methyl iodide are heated at 80° C. for 2 h in 50 ml of dimethylformamide, and the mixture is poured into 500 ml of water at room temperature and extracted three times with 150 ml of ether. The combined organic phases are washed with water and dried using sodium sulphate. After distilling off the solvent in vacuo, 11.1 g are obtained.

Crude yield: 95.2% of theory Melting point: 83° C.

EXAMPLE 6

Ethyl 4-(4-fluorophenyl)-3-hydroxymethyl-6-isopropyl-2-methoxy-pyridine-5-carboxylate

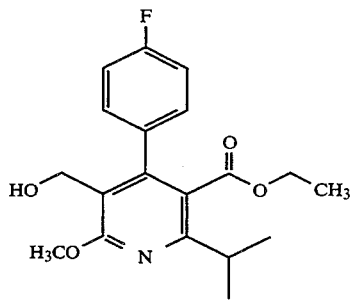

1.48 g (3.95 mmol) of the compound from Example 5 are dissolved in 30 ml of toluene, the solution is cooled to −78° C. under nitrogen and 6.6 ml (10 mmol) of a 1.5 molar solution of diisobutylaluminium hydride in toluene are added dropwise at this temperature. The cooling bath is removed and the mixture is stirred at room temperature for 2 h. After hydrolysis using 20% strength aqueous potassium sodium tartrate solution, the organic phase is separated off, the aqueous phase is washed three times with toluene, and the combined organic phases are washed with saturated sodium chloride solution and dried using sodium sulphate.

After distilling off the solvent in vacuo, 1.52 g of oil are obtained, which is chromatographed on silica gel (ethyl acetate/petroleum ether 1:5).

Yield: 520 mg (38% of theory) and 310 mg (21%) of starting product.

EXAMPLE 7

Ethyl 4-(4-fluorophenyl)-6-isopropyl-3-methoxymethyl-2-methoxy-pyridine-5-carboxylate

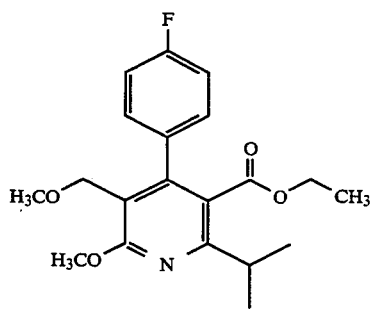

520 mg (1.5 mmol) of the compound from Example 6 are stirred at room temperature for 4 h in 42 mg (1.75 mmol) of sodium hydride and 0.3 ml (4.5 mmol) of methyl iodide in 4 ml of dimethylformamide. The reaction mixture is poured into ice-water, washed three times with ether, and the combined ether phases are washed with water and saturated sodium chloride solution and dried using sodium sulphate. After removal of the solvent in a rotary evaporator 520 mg of oil are obtained.

Yield: 100% of theory.

EXAMPLE 8

4-(4-Fluorophenyl)-5-hydroxymethyl-6-isopropyl-2-methoxy-3-methoxy-methylpyridine

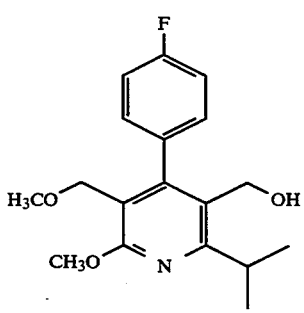

1.19 g (3.5 mmol) of the compound from Example 7 were reduced with 5.2 ml (7.7 mmol) of a 1.5 molar solution of diisobutylaluminium hydride in toluene analogously to Example 6. After chromatography on silica gel (ethyl acetate/petroleum ether 1:5), 730 mg of solid are obtained.

Yield: 66% of theory Melting Point:

EXAMPLE 9

4-(4-Fluorophenyl)-6-isopropyl-2-methoxy-3-methoxymethyl-pyridine-5-carbaldehyde

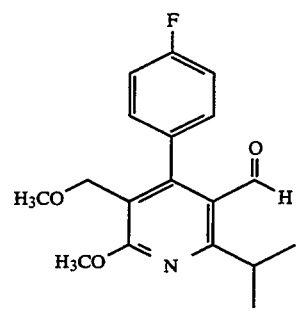

568 mg (2.64 mmol) of pyridinium chlorochromate are added to a solution of 0.7 g (2.2 mmol) of the compound from Example 8 in 120 ml of methylene chloride, the mixture is stirred overnight at room temperature, filtered off with suction through kieselguhr and washed with 200 ml of methylene chloride, filtered off with suction through silica gel, washed with 200 ml of methylene chloride and dried using sodium sulphate, and 670 mg of oil are obtained after removal of the solvent in a rotary evaporator.

Yield: 96% of theory.

EXAMPLE 10

(E)-3-[4-(4-Fluorophenyl)-6-isopropyl-2-methoxy-3-methoxymethyl-pyridin-5-yl]-prop-2-enal

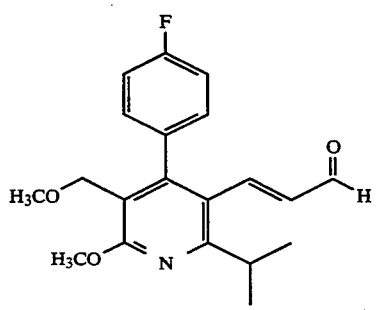

804 (3.1 mmol) of diethyl 2-(cyclohexylamino)-vinylphosphate dissolved in 6 ml of dry tetrahydrofuran are added dropwise under nitrogen to a suspension of 59 mg (2.5 mmol) of sodium hydride in 6 ml of dry tetrahydrofuran at −5° C. After 30 min, 0.65 g (2.05 mmol) of the compound from Example 9 in 15 ml of dry tetrahydrofuran is added dropwise at the same temperature and the mixture is heated to reflux for 30 min. After cooling to room temperature, the mixture is added to 200 ml of ice-cold water and extracted three times using 100 ml of ethyl acetate each time. The combined organic phases are washed with saturated sodium chloride solution and dried over sodium sulphate. After concentration in vacuo, the residue is taken up in 5 ml of toluene, treated with a solution of 0.9 g (7 mmol) of oxalic acid dihydrate in 12 ml of water and heated to reflux for 90 min. After cooling to room temperature, the phases are separated, and the organic phase is washed with saturated sodium chloride solution, dried over sodium sulphate and concentrated in vacuo. The residue is dissolved in methylene chloride and filtered through silica gel.

Yield: 560 mg of solid (79.6% of theory).

EXAMPLE 11

Methyl (E)-7-[4-(4-fluorophenyl)-6-isopropyl-2-methoxy-3-methoxy-methyl-pyridin-5-yl]-5-hydroxy-3-oxo-hept-6-enoate

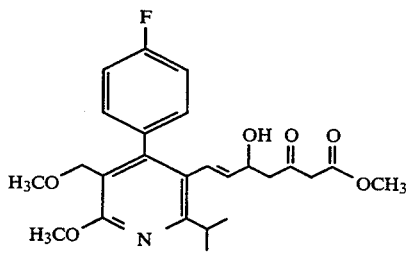

0.35 ml (3.3 mmol) of methyl acetoacetate are added dropwise under nitrogen to a suspension of 80 mg (3.4 mmol) of sodium hydride in 3 ml of dry tetrahydrofuran at −5° C. After 15 min, 2.3 ml (3.3 mmol) of 15% strength butyllithium in n-hexane and 3.3 ml (3.3 mmol) of a 1 molar zinc chloride solution in ether are added dropwise at the same temperature and the mixture is stirred for 15 min. 530 mg (1.5 mmol) of the compound from Example 10 dissolved in 8 ml of dry tetrahydrofuran are then added dropwise and the mixture is stirred at −5° C. for 30 min. The reaction solution is cautiously diluted with 100 ml of saturated aqueous ammonium chloride solution and the mixture is extracted three times with 100 ml of ether each time. The combined organic phases are washed twice with saturated sodium hydrogen carbonate solution and once with saturated sodium chloride solution, dried over sodium sulphate and concentrated in vacuo.

Crude yield: 760 mg (100% of theory).

EXAMPLE 12

Methyl erythro-(E)-7-[4-(4-fluorophenyl)-6-isopropyl-2-methoxy-3-methoxymethyl-pyridin-5-yl]-3,5-dihydroxy-hept-6-enoate

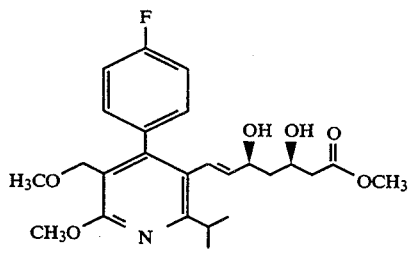

1.9 ml (1.9 mmol) of 1M triethylborane solution in tetrahydrofuran are added at room temperature to a solution of 730 mg (1.6 mmol) of the compound from Example 11 in 13 ml of dry tetrahydrofuran, air is passed through the solution for 5 min and it is cooled to an internal temperature of −30° C. 72 mg (1.9 mmol) of sodium borohydride and, slowly, 1.3 ml of methanol are added, the mixture is stirred at −30° C. for 30 min and then treated with a mixture of 5 ml of 30% strength hydrogen peroxide and 11 ml of water. The temperature is allowed to rise to 0° C. during the course of this and the mixture is stirred for a further 30 min. The mixture is extracted three times with 70 ml of ethyl acetate each time, the combined organic phases are washed once each with 10% strength potassium iodide solution, 10% strength sodium thiosulphate solution, saturated sodium hydrogen carbonate solution and saturated sodium chloride solution, dried over sodium sulphate and concentrated in vacuo. The residue is chromatographed on a column (100 g of silica gel 230–400 mesh, ethyl acetate/petroleum ether 1:2).

Yield: 350 mg of oil (47.6% of theory).

EXAMPLE 13

Ethyl 3-(tert-butyldimethylsilyloxymethyl)-4-(4-fluorophenyl)-6-isopropyl-2-methoxy-pyridine-5-carboxylate

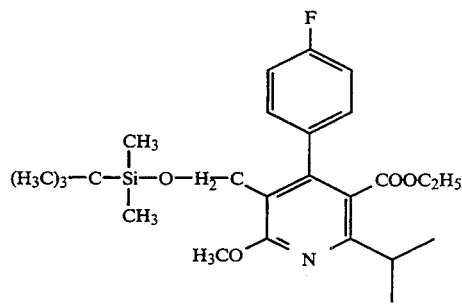

304 mg (2 mmol) of tert-butyldimethylsilyl chloride, 262 mg (4 mmol) of imidazole and 0.05 g of 4-dimethylaminopyridine are added at room temperature to a solution of 600 mg (1.8 mmol) of the compound from Example 6 in 20 ml of dimethylformamide. The mixture is stirred overnight at room temperature, treated with 200 ml of water and adjusted to pH 3 using 1N hydrochloric acid. The mixture is extracted three times using 100 ml of ether each time, and the combined organic phases are washed once with saturated sodium chloride solution, dried over magnesium sulphate and concentrated in vacuo. The residue is chromatographed on a column (150 g of silica gel, 70–230 mesh, $\phi$4 cm, using ethyl acetate/petroleum ether 1:9).

Yield: 700 mg (87% of theory).

EXAMPLE 14

Methyl erythro-(E)-7-[3-tert-butyldimethylsilyloxymethyl-4-(4-fluorophenyl)-6-isopropyl-2-methoxy-pyridin-5-yl]-3,5-dihydroxy-hept-6-enoate

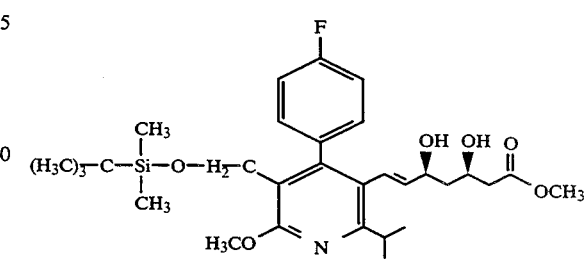

Starting from Example 13, the title compound was prepared analogously to the procedures of Examples 8–12.

EXAMPLE 15

Methyl erythro-(E)-7-[4-(4-fluorophenyl)-3-hydroxymethyl-6-isopropyl-2-methoxy-pyridin-5-yl]-3,5-dihydroxy-hept-6-enoate

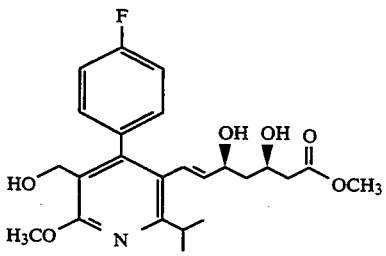

100 mg (0.18 mmol) of the compound from Example 14 are stirred at room temperature overnight in a solution of 1 ml of 1N hydrochloric acid and 9 ml of methanol. After concentration, the residue is taken up using methylene chloride, washed with saturated sodium hydrogen carbonate solution, dried and filtered through silica gel (ethyl acetate/petroleum ether 1:1).

Yield: 46 mg (57% of theory) Melting point:

PREPARATION EXAMPLES

EXAMPLE I 3S,5S-(+)-(E)-7-[4-(4-Fluorophenyl)-6-isopropyl-2-methoxy-3-methoxymethyl-pyrid-5-yl]-hept-6-ene-1,3,5-triol

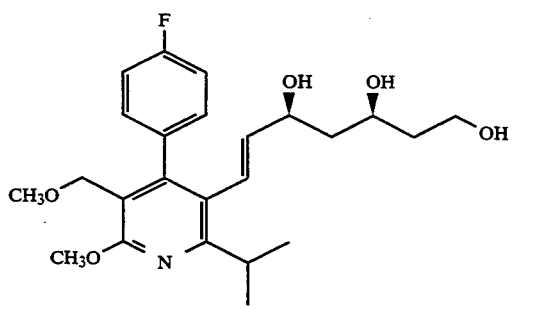

3.92 g (8.5 mmol) of 3R,5S-(+)-methyl (E)-7-[4-(4-fluorophenyl)-6-isopropyl-2-methoxy-3-methoxymethyl-pyrid-5-yl]-3,5-dihydroxy-hept-6-enoate are dissolved in 100 ml of absolute THF under argon. 35.8 ml (43 mmol) of a 1.2M diisobutylaluminium hydride solution (in toluene) are added dropwise at −78° C. After 12 h at −30° C., the reaction solution is allowed to come to 0° C. and 150 ml of water are cautiously added. The mixture is then extracted three times with 200 ml of ethyl acetate each time. The organic phase is washed with saturated NaCl solution, dried using $Na_2SO_4$ and concentrated in a rotary evaporator. The desired product is obtained after chromatography on silica gel 60 (25–40μ, eluent ethyl acetate/petroleum ether 7:3).

Yield: 1.54 g (42% of theory) $^1$H NMR (CDCl$_3$): δ=1.22 (m, 6H); 1.43 (m, 2H); 1.62 (m, 2H); 3.22 (s, 3H); 3.25 (sept. 1H); 3.84 (m, 2H); 4.01 (s, 3H); 4.04 (m, 1H); 4.06 (s, 2H); 4.28 (m, 1H); 5.22 (dd, 1H); 6.25 (d, 1H); 7.0–7.2 (m, 4H) ppm.

EXAMPLE II 3S,5S-(+)-(E)-7-[4-(4-Fluorophenyl)-3-hydroxymethyl-6-isopropyl-2-methoxy-pyrid-5-yl]-hept-6-ene-1,3,5-triol

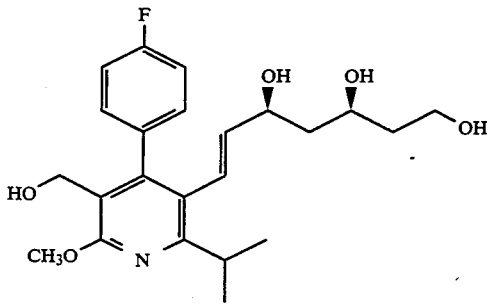

Preparation is carried out analogously to Example I starting from 3R,5S-(+)-methyl (E)-7-[4-(4-fluorophenyl)-3-hydroxymethyl-6-isopropyl-2-methoxy-pyrid-5-yl]-3,5-dihydroxy-hept-6-enoate.

$^1$H NMR (CDCl$_3$): δ=1.25 (d, 6H); 1.42 (m, 2H); 1.63 (m, 2H); 3.28 (sept. 1H); 3.82 (m, 2H); 4.01 (m, 1H); 4.06 (s, 3H); 4.27 (m, 1H); 4.35 (d, 2H); 5.23 (dd, 1H); 6.22 (d, 1H); 7.0–7.2 (m, 4H) ppm.

We claim:
1. Substituted 4-phenyl-pyridones and 4-phenyl-2-alkoxypyridines of the general formula

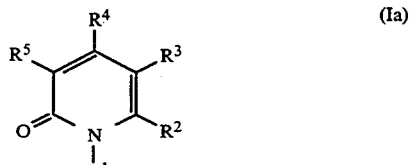

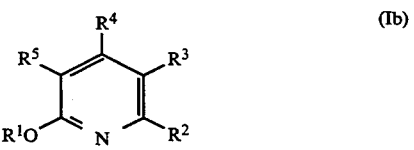

in which
$R^1$ represents straight-chain or branched alkyl having up to 8 carbon atoms,
$R^2$ represents cycloalkyl having 3 to 7 carbon atoms, or represents straight-chain or branched alkyl having up to 8 carbon atoms,
$R^3$ represents a radical of the formula

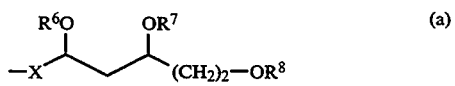

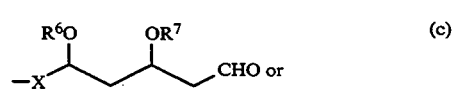

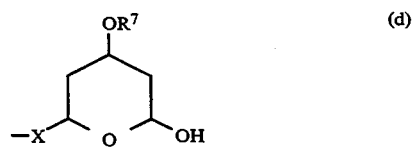

in which
  X denotes the group —CH$_2$—CH$_2$—, —CH=CH— or —C≡C—, and
  R$^6$, R$^7$ and R$^8$ are identical or different and denote hydrogen or a radical of the formula —CO—R$^9$ or —COOR$^{10}$, in which
    R$^9$ and R$^{10}$ are identical or different and denote straight-chain or branched alkyl having up to 8 carbon atoms, or phenyl,
  or
  R$^6$ and R$^7$ together form a radical of the formula

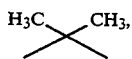

R$^4$ represents phenyl which is optionally substituted up to 2 times by identical or different halogen, trifluoromethyl, methoxy, phenoxy or straight-chain or branched alkyl having up to 8 carbon atoms,
  R$^5$ has the abovementioned meaning of R$^3$ and is identical to or different from this, or represents hydrogen, cyano, carboxyl or straight-chain or branched alkoxycarbonyl having up to 8 carbon atoms, or represents straight-chain or branched alkyl having up to 8 carbon atoms, which is optionally substituted by halogen, hydroxyl, by straight-chain or branched alkoxy having up to 8 carbon atoms, or by a group of the formula —O—(CH$_2$)$_a$—R$^{11}$ or —O—CO—R$^{12}$, in which
    a denotes a number 0 or 1,
    R$^{11}$ denotes phenyl or benzyl, each of which is optionally substituted up to 2 times in the aromatic system by identical or different halogen, trifluoromethyl, cyano, nitro or straight-chain or branched alkyl having up to 6 carbon atoms,
    R$^{12}$ has the abovementioned meaning of R$^{11}$ and is identical to or different from this, or denotes straight-chain or branched alkyl having up to 8 carbon atoms, or
  R$^5$ represents a radical of the formula —CH=N—O—R$^{13}$, in which
    R$^{13}$ has the abovementioned meaning of R$^{12}$ and is identical to or different from this.

2. Substituted 4-phenyl-pyridones and 4-phenyl-2-alkoxypyridines according to claim 1, in which
  R$^1$ represents straight-chain or branched alkyl having up to 6 carbon atoms,
  R$^2$ represents cyclopropyl, cyclopentyl or cyclohexyl, or represents straight-chain or branched alkyl having up to 6 carbon atoms,
  R$^3$ represents a radical of the formula

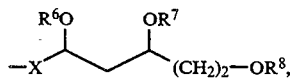

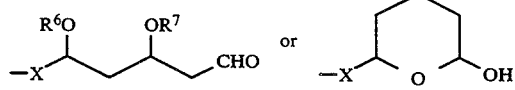

in which
  X denotes the group —CH$_2$—CH$_2$—, —CH=CH— or —C≡C—,
  R$^6$, R$^7$ and R$^8$ are identical or different and denote hydrogen or a radical of the formula —CO—R$^9$ or —COO—R$^{10}$, in which
    R$^9$ and R$^{10}$ are identical or different and denote straight-chain or branched alkyl having up to 6 carbon atoms, or phenyl,
  or
  R$^6$ and R$^7$ together form a radical of the formula

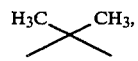

R$^4$ represents phenyl which is optionally substituted up to 2 times by identical or different fluorine, chorine, bromine, trifluoromethyl or straight-chain or branched alkyl having up to 6 carbon atoms,
  R$^5$ has the abovementioned meaning of R$^3$ and is identical to or different from this, or represents hydrogen, cyano, carboxyl or straight-chain or branched alkoxycarbonyl having up to 6 carbon atoms, or represents straight-chain or branched alkyl having up to 6 carbon atoms, which is optionally substituted by fluorine, chlorine, bromine, hydroxyl or by straight-chain or branched alkoxy having up to 6 carbon atoms, or which is substituted by a group of the formula —O—(CH$_2$)$_a$—R$^{11}$ or —O—CO—R$^{12}$, in which
    a denotes a number 0 or 1, and
    R$^{11}$ denotes phenyl or benzyl, each of which is optionally substituted in the aromatic system by fluorine, chlorine, bromine, trifluoromethyl, cyano, nitro or straight-chain or branched alkyl having up to 4 carbon atoms,
    R$^{12}$ has the abovementioned meaning of R$^{11}$ and is identical to or different from this, or denotes straight-chain or branched alkyl having up to 6 carbon atoms,
  or
  R$^5$ represents a radical of the formula —CH=N—O—R$^{13}$, in which
    R$^{13}$ has the abovementioned meaning of R$^{12}$ and is identical to or different from this.

3. Substituted 4-phenyl-pyridones and 4-phenyl-2-alkoxypyridines according to claim 1, in which
  R$^1$ represents straight-chain or branched alkyl having up to 4 carbon atoms,
  R$^2$ represents cyclopropyl or represents straight-chain or branched alkyl having up to 4 carbon atoms,
  R$^3$ represents a radical of the formula

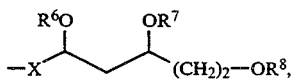

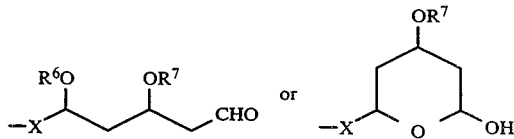

in which
  X denotes the group —CH$_2$—CH$_2$— or —CH=CH—,
  R$^6$, R$^7$ and R$^8$ are identical or different and denote hydrogen or a radical of the formula —CO—R$^9$, in which R⁹ denotes straight-chain or branched alkyl having up to 4 carbon atoms, R⁴ represents phenyl which is optionally substituted by fluorine, trifluoromethyl or by straight-chain or branched alkyl having up to 4 carbon atoms, R⁵ has the abovementioned meaning of R³ and is identical to or different from this, or represents hydrogen or represents straight-chain or branched alkyl having up to 4 carbon atoms, which is optionally substituted by hydroxyl or by straight-chain or branched alkoxy having up to 4 carbon atoms.

4. Substituted 4-phenyl-pyridones and 4-phenyl-2-alkoxypyridines according to claim 1, in which R¹ represents straight-chain or branched alkyl having up to 4 carbon atoms, R² represents cyclopropyl or represents straight-chain or branched alkyl having up to 4 carbon atoms, R³ represents a radical of the formula

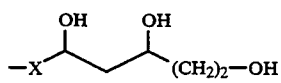

in which

X denotes the group —CH₂—CH₂— or —CH=CH—,

R⁴ represents phenyl which is optionally substituted by fluorine, and

R⁵ has the abovementioned meaning of R³ or represents straight-chain or branched alkyl having up to 4 carbon atoms, which is optionally substituted by hydroxyl or alkoxy having up to four carbon atoms.

5. A compound according to claim 1 wherein such compound is 3S,5S-(+)-(E)-7-[4-(4-fluorophenyl)-6-isopropyl-2-methoxy-3-methoxymethylpyrid-5-yl]-hept-6-ene-1,3,5triol of the formula

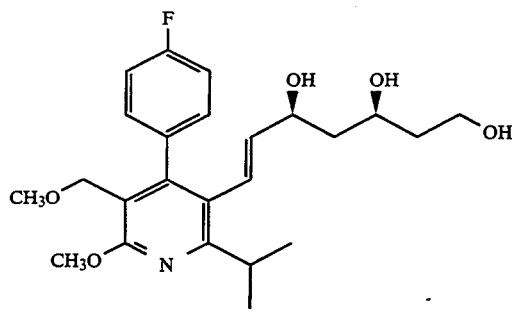

6. A compound according to claim 1 wherein such compound is 3S,5S-(+)-(E)-7-[4-(4-fluorophenyl)-3-hydroxymethyl-6-isopropyl-2-methoxypyrid-5-yl]-hept-6-ene-1,3,5-triol of the formula

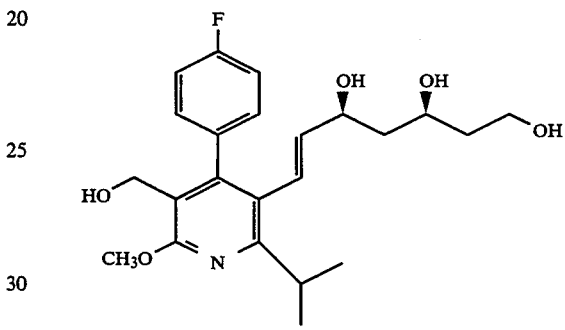

7. A composition for the treatment of hyperlipoproteinae and arteriosclerosis comprising an amount effective therefor of a compound according to claim 1 and a pharmacologically acceptable diluent.

8. The method of treating hyperlipoproteinaemia and arteriosclerosis in a patient in need thereof which comprises administering to such patient an amount effective therefor of a compound according to claim 1.

* * * * *